(12) United States Patent
Nanda

(10) Patent No.: US 7,385,098 B2
(45) Date of Patent: Jun. 10, 2008

(54) AROMATICS ALKYLATION PROCESS

(75) Inventor: Vijay Nanda, Houston, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 43 days.

(21) Appl. No.: 11/546,678

(22) Filed: Oct. 12, 2006

(65) Prior Publication Data

US 2007/0038009 A1 Feb. 15, 2007

Related U.S. Application Data

(63) Continuation-in-part of application No. 10/722,790, filed on Nov. 25, 2003, now Pat. No. 7,141,710.

(51) Int. Cl.
*C07C 2/66* (2006.01)
(52) U.S. Cl. ........................ 585/467; 585/323
(58) Field of Classification Search ................ 585/467, 585/323
See application file for complete search history.

(56) References Cited

U.S. PATENT DOCUMENTS

| 3,751,506 | A | 8/1973 | Buress | 260/671 R |
| 4,107,224 | A | 8/1978 | Dwyer | 260/671 R |
| 5,998,687 | A | 12/1999 | Woodle et al. | 585/449 |
| 6,057,485 | A | 5/2000 | Merrill et al. | 585/449 |
| 6,090,991 | A | 7/2000 | Butler et al. | 585/467 |

OTHER PUBLICATIONS

Williams, P.T. et al., "Catalytic pyrolysis of tyres: influence of catalyst temperature", Fuel, IPC Science and Technology Press, Guildford, Great Britain, vol. 81, No. 18, Dec. 2002, pp. 2425-2434, XP004380934.

*Primary Examiner*—Thuan Dinh Dang
(74) *Attorney, Agent, or Firm*—Darryl Tyus

(57) ABSTRACT

The invention relates to a process for producing alkylated aromatics, preferably ethylbenzene, in a multiple bed reactor in which at least two catalysts, each comprising a molecular sieve, are used in sequential beds. The first alkylation catalyst is selected to have a higher activity or alpha value than the subsequent alkylation catalyst.

24 Claims, 1 Drawing Sheet

AROMATICS ALKYLATION PROCESS

PRIORITY CLAIM

This application is a continuation in part of U.S. Ser. No. 10/722,790, filed Nov. 25, 2003 now U.S. Pat. No. 7,141,710, the disclosures of which are incorporated herein by reference in its entirety.

FIELD OF THE INVENTION

The present invention relates to a process for improving the efficiency and reducing certain byproducts in alkylation of aromatic compounds to produce mono-alkylaromatic compounds. In particular, vapor phase alkylation of benzene to produce ethylbenzene can be accomplished with increased ethylbenzene purity and reduced ethylene and benzene loss to byproduct formation. Alternatively, the capacity of an existing process can be increased while maintaining product specifications.

BACKGROUND OF THE INVENTION

A variety of processes for converting aromatics in the presence of molecular sieve catalysts are known in the chemical processing industry. Aromatic conversion reactions include alkylation and transalkylation to produce alkylaromatics such as ethylbenzene (EB), ethyltoluene, cumene and higher aromatics. An alkylation reactor which produces a mixture of mono- and poly-alkylaromatic compounds may be linked in some way with a transalkylation reactor to maximize the net production of mono-alkylaromatic compounds. Such alkylation and transalkylation conversion processes can be carried out in the liquid phase, in the vapor phase, or under conditions in which both liquid and vapor phases are present. The preferred catalysts and the byproduct formation differ with the severity of reaction conditions and the phase conditions in which the reaction is carried out.

In efforts to improve commercial alkylation operations, emphasis is placed not only on the conversion efficiency of the catalyst but also on the selectivity of the catalyst, including reduced production of certain byproducts. For example, in the manufacture of ethylbenzene, ethylene and benzene are introduced into an alkylation reactor in the presence of various catalysts. Some of the byproducts include diethylbenzenes, xylenes, propylbenzene, cumene, butylbenzene, and other components referred to collectively as heavies. Production of unwanted byproducts increases feedstock usage as well as the cost of separating such unwanted byproducts. Byproducts which are not removed can materially impact the efficiency of downstream operations, such as the dehydrogenation of EB to form styrene monomer.

It has been shown that zeolites like ZSM-5 show high activity and selectivity for vapor phase alkylation of benzene with ethylene and that catalysts of this type in the acid form remain active for unusually long periods between regenerations. Discussion of acid zeolite ZSM-5 for vapor phase alkylation is provided in U.S. Pat. No. 3,751,506, which is herein fully incorporated by reference and which describes control of the exothermic heat of reaction by conducting the reaction in a series of reactors with intermediate cooling and addition of ethylene between stages.

Another process for vapor phase alkylation is described in U.S. Pat. No. 4,107,224, which is herein fully incorporated by reference. Benzene and dilute ethylene are reacted in vapor phase over a solid porous catalyst selected from ZSM-5, ZSM-11, ZSM-12, ZSM-35, ZSM-38, and other similar materials in a series of reaction zones with intermediate injection of cold reactants and diluent to control temperature.

U.S. Pat. No. 6,090,991, which is herein fully incorporated by reference, describes vapor phase ethylbenzene production in which a feedstock containing benzene and ethylene is applied to an alkylation reaction zone having at least one catalyst bed containing a monoclinic silicalite catalyst having a weak acid site concentration of less than 50 micromoles per gram.

U.S. Pat. No. 6,057,485, which is herein fully incorporated by reference, describes vapor phase ethylbenzene production by alkylation over a split load of monoclinic silicalite alkylation catalysts having different silica/alumina ratios. A feedstock containing benzene and ethylene is applied to a multi-stage alkylation reaction zone having a plurality of series-connected catalyst beds. At least one catalyst bed contains a first monoclinic silicalite catalyst having a silica/alumina ratio of at least 275. At least one other catalyst bed contains a second monoclinic silicalite catalyst having a silica/alumina ratio of less than about 275.

U.S. Pat. No. 5,998,687, which is herein fully incorporated by reference, describes ethylbenzene production by alkylation over a stacked reactor loaded with zeolite beta followed by zeolite Y to reduce overall flux oil production.

A disadvantage of vapor phase alkylation reactions is the formation of polyalkylated byproducts. While the art currently provides for various transalkylation processes to handle some of the alkylation byproducts such as diethylbenzene, it would be desirable to reduce the production of byproducts, especially byproducts that are not easily handled in an alkylation/transalkylation process. It would also be desirable to reduce the quantity of reactants consumed in production of byproducts Recently, catalysts have been developed which allow the alkylation reactions to be carried out in the liquid phase alkylation at relatively mild reaction conditions. The reduced temperature associated with operating in the liquid phase allows for a significant reduction in undesirable by-products.

In existing facilities designed for vapor phase reactions, it can be cost-prohibitive to retrofit for a liquid phase operation unless a substantial increase in production capacity is required. Improved catalysts allowing lower temperature operation in such vapor phase facilities are highly desirable.

SUMMARY OF THE INVENTION

In one embodiment, this invention is a process for alkylating an aromatic hydrocarbon reactant with an alkylating agent to produce an alkylated aromatic product, said process comprising:

(a) introducing said aromatic hydrocarbon reactant and said alkylating agent into a reactor unit containing a plurality of sequentially arranged beds comprised of a first bed containing a first catalyst effective for alkylating said aromatic hydrocarbon reactant and a second bed downstream from said first bed and containing a second catalyst effective for alkylating said aromatic hydrocarbon reactant and having less catalytic activity than said first catalyst;

(b) alkylating in said first bed under alkylation conditions said aromatic hydrocarbon reactant with said alkylating agent to form a first effluent comprising a mono-alkylaromatic compound, an unreacted portion of the aromatic hydrocarbon reactant, and polyalkylated aromatic compounds, (c) alkylating in said second bed under alkylation conditions at least a portion of said unreacted aromatic hydrocarbon reactant present in said effluent with said alkylating agent to form a product effluent, and (d) removing said product effluent from said reactor unit, said product effluent comprising a mono-alkylaromatic compound, an unreacted portion of the aromatic hydrocarbon reactant, and polyalkylated aromatic compounds.

In another embodiment, this invention can be a process for the vapor-phase ethylation of benzene comprising a) providing a multi-stage alkylation reaction zone having a plurality of series-connected catalyst beds, at least one of the series-connected catalyst beds containing a first alkylation catalyst comprising a zeolite and at least one subsequent catalyst bed containing a second alkylation catalyst comprising a zeolite, the first alkylation catalyst being more active for the ethylation of benzene than the second alkylation catalyst, b) introducing a feedstock of benzene and ethylene into the multistage alkylation reaction zone;

c) operating the multistage alkylation reaction zone at temperature and pressure conditions in which the benzene is in a vapor phase to cause vapor-phase ethylation of the benzene in the presence of the first and second alkylation catalysts to produce an alkylation product comprising a mixture of ethylbenzene and polyalkylated aromatic components; and d) withdrawing the alkylation product from the multistage alkylation reaction zone.

In yet another embodiment, this invention can be either of the processes above with the additional steps of separating the polyalkylated aromatic components from the alkylation product and supplying at least a portion of the polyalkylated aromatic component along with benzene to a transalkylation reaction zone operated in the vapor or liquid phase under temperature and pressure conditions sufficient to cause transalkylation of the polyalkylated aromatic fraction to produce a transalkylation product having an enhanced ethylbenzene content and a reduced polyalkylated aromatic components content.

In a further alternative embodiment, the invention can be any of the processes above, further including the steps of separating the polyalkylated aromatic components from the alkylation product; and supplying at least a portion of the polyalkylated aromatic component to the alkylation reaction zone to cause transalkylation of the polyalkylated aromatic fraction to produce a transalkylation product having an enhanced ethylbenzene content and a reduced polyalkylated aromatic components content.

DETAILED DESCRIPTION OF THE INVENTION

Introduction

Figure 1:
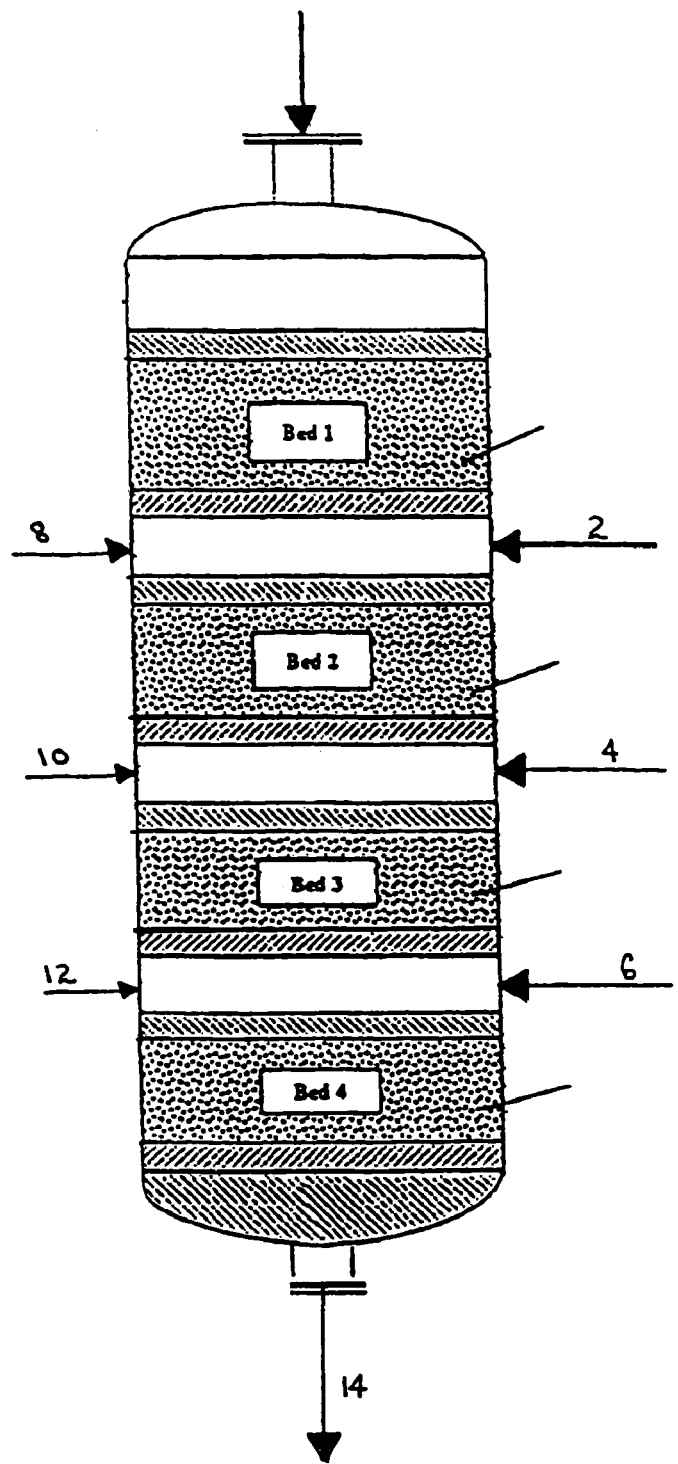
FIG. 1 shows the general configuration of a reactor containing four catalyst beds.

Aromatics alkylation reactions are highly exothermic, and many reaction schemes have been developed to control temperature rise through the reactor in an effort to minimize byproduct formation. One such solution has been the interstage introduction of lower temperature aromatic reactant feed streams to both act as a reactant and a to reduce the temperature by producing a quenching effect. In most current vapor phase aromatics alkylation reaction systems, multiple beds of the same catalyst are used sequentially for alkylaromatic production. For example, in a typical ethylbenzene reactor which operates with between four and eight catalyst beds, only about 50 to 65% of the benzene feed can be directed towards the top bed (reactor inlet). The remaining benzene is added between the catalyst beds as a heat sink for temperature control (quenching) purposes, since each bed operates optimally at essentially the same inlet temperature. This mode of operation generally causes the lowest and highest benzene to ethylene ratios to occur in the top and bottom beds respectively. The lower benzene flow in bed 1 of the reactor leads to higher by-products formation due to reduced localized benzene to ethylene ratio and higher temperature rise across the catalyst bed.

This invention provides for an improved process for the production of alkylaromatics by contacting the reactants in a reaction zone maintained under such conditions that the reaction occurs in the vapor phase and in the presence of at least two catalysts exhibiting different activity. This allows the reaction zone, comprising a series of catalyst beds, to operate at more varied temperatures and can reduce or eliminate the need for quenching or otherwise cooling the effluent from each stage.

Arranging the catalyst in the alkylation reactor such that the highest activity catalyst is in one or more upper bed(s) and the lowest activity catalyst is in one or more later bed(s) allows the beds to operate at more varied inlet temperatures. It would now be preferable to have a rising temperature profile as the aromatic compound, for example benzene, and the alkylating agent, for example ethylene, flow through the reactor.

FIG. 1 shows a simplified four-bed reactor, in which the feed to the first catalyst bed 1 is a mixture of the aromatic reactant and the alkylating agent. Additional alkylating agent 2 and optionally additional aromatic reactant 8 are combined with the effluent from the first bed and introduced to the second catalyst bed. Again, additional alkylating agent 4 and optionally additional aromatic reactant 10 are combined with the effluent from the second bed and introduced to the third catalyst bed. The same steps are repeated with additional alkylating agent 6 and optionally additional aromatic reactant 12 being combined with the effluent from the third catalyst bed and introduced to the fourth catalyst bed. The effluent from the fourth catalyst bed 14 comprises a mono-alkylated aromatic compound, unreacted aromatic reactant, and poly-alkylated aromatic compounds. In the processes of the invention, at least the first bed, and optionally up to the first three beds contain a higher activity alkylation catalyst, and the input of aromatic reactant is shifted from inlets 8, 10, and/or 12 to inlet 1.

In one embodiment where the aromatic hydrocarbon reactant is benzene and the alkylating agent is ethylene, this catalyst arrangement would allow more of the benzene, preferably greater than 60 wt. % of the total, more preferably greater than 80 wt. %, and most preferably 100%, to be directed toward the top (first) bed, resulting in an increased localized benzene to ethylene ratio and reduced temperature rise across the upper catalyst bed in a downflow arrangement. This improvement would result in both improved process yield and reduced byproduct formation, particularly reduced formation of byproducts not easily transalkylated to form ethylbenzene.

In one embodiment of the present invention, highest activity catalyst is loaded into the top (first) bed(s) and lowest activity catalyst is loaded into the bottom bed(s). This allows the top bed to operate at the lowest inlet temperature and the catalyst temperature increases progressively as the reactants move towards the lower beds. This catalyst arrangement requires little or no quench benzene to be added interstage between the beds for temperature control purposes. The quench benzene can be diverted towards the top catalyst bed, thereby increasing both the overall (benzene and ethylene) weight hourly space velocity (WHSV) and the localized benzene to ethylene ratio through the upper catalyst beds. This benzene shift provides a severity compensation for the higher activity catalyst beds and also reduces the temperature increase across these beds due to a lower ethylene concentration. Product purity is improved by operating at a higher localized benzene to ethylene ratio, higher overall WHSV, and lower temperatures both at the inlet and within the catalyst beds. Reduced decline in catalyst activity relative to throughput is an additional unexpected benefit of this invention.

In an alternative embodiment, staging a higher activity catalyst in a first catalyst bed with a lower activity catalyst in a second catalyst bed can also be used to increase the capacity of a process configuration without increasing the overall aromatic reactant circulation and the associated increased production of undesirable byproducts.

Catalysts suitable for vapor phase alkylation of aromatics include a variety of molecular sieves, particularly aluminosilicate zeolites, which are classified by framework type and described by the Structure Commission of the International Zeolite Association according to the rules of the IUPAC Commission on Zeolite Nomenclature. A framework-type describes the topology and connectivity of the tetrahedrally coordinated atoms constituting the framework and makes an abstraction of the specific properties for those materials. Molecular sieves for which a structure has been established are assigned a three letter code and are described in the *Atlas of Zeolite Framework Types,* 5th edition, Elsevier, London, England (2001), which is herein fully incorporated by reference.

Other molecular sieves include those described in R. Szostak, *Handbook of Molecular Sieves,* Van Nostrand Reinhold, New York, N.Y. (1992), which is herein fully incorporated by reference.

Molecular sieves preferred for use in the catalysts of this invention are those having intermediate pore sizes, preferably having a pore dimension from about 5 Angstroms to about 7 Angstroms. Examples of suitable molecular sieve materials for use in the alkylation catalysts of this invention include, but are not limited to, ZSM-5, described in U.S. Pat. No. 3,702,886; ZSM-11, described in U.S. Pat. No. 3,709,979; ZSM-12, described in U.S. Pat. No. 3,832,449; ZSM-35, described in U.S. Pat. No. 4,016,245; and ZSM-38, described in U.S. Pat. No. 4,046,859.

In practicing a particular desired chemical conversion process, it may be useful to incorporate any of the above-described crystalline zeolites with a matrix or binder comprising another material resistant to the temperature and other conditions employed in the process.

Useful matrix materials include both synthetic and naturally occurring substances, as well as inorganic materials such as clay, silica and/or metal oxides. The latter may be either naturally occurring or in the form of gelatinous precipitates or gels including mixtures of silica and metal oxides. Naturally occurring clays which can be composited with the zeolite include those of the montmorillonite and kaolin families, which families include the sub-bentonites and the kaolins commonly known as Dixie, McNamee-Georgia and Florida clays or others in which the main mineral constituent is halloysite, kaolinite, dickite, nacrite, or anauxite. Such clays can be used in the raw state as originally mined or initially subjected to calcination, acid treatment, or chemical modification.

In addition to the foregoing materials, the zeolites employed herein may be composited with a porous matrix material, such as alumina, silica-alumina, silica-magnesia, silica-zirconia, silica-thoria, silica-beryllia, and silica-titania, as well as ternary compositions, such as silica-alumina-thoria, silica-alumina-zirconia, silica-alumina-magnesia and silica-magnesia-zirconia. The matrix may be in the form of a cogel. The relative proportions of zeolite component and inorganic oxide gel matrix, on an anhydrous basis, may vary widely with the zeolite content ranging from between about 1 to about 99 percent by weight and more usually in the range of about 5 to about 80 percent by weight of the dry composite.

Activity of a catalyst can be impacted by various factors including the synthesis method, silica/alumina ratio, selection of binder, shape of the extruded particles, steaming, and other treatments. One measurement of relative activity of catalysts for certain kinds of reactions is the alpha value. Catalytic activity of zeolites, such as ZSM-5, is often reported using alpha value, which compares the catalytic cracking activity of the catalyst (rate of normal hexane conversion per volume of catalyst per unit time) with the activity of a standard silica-alumina cracking catalyst. The alpha test is described in U.S. Pat. No. 3,354,078; in the Journal of Catalysis, Vol. 4, p. 527 (1965); Vol. 6, p. 278 (1966); and Vol. 61, p. 395 (1980). The experimental conditions of the test used herein include a constant temperature of 538° C. and a variable flow rate as described in detail in the Journal of Catalysis, Vol. 61, p. 395.

For aluminosilicate zeolites such as ZSM-5, the alpha value generally decreases with increasing silica/alumina ratio in the synthesized zeolite. Preferred silica/alumina ratios for the catalysts of the present invention are less than 200:1, more preferably less than 100:1, and most preferably from about 12:1 to about 80:1. Other variables which have been found to impact the activity of the zeolite are the crystal size and the selection of binder material. The alpha value of an as-synthesized zeolite or a catalyst composition can be reduced for a specific application through a variety of treatment methods.

Alpha value is a better indicator of catalyst activity for some reactions than for others. For the purposes of this invention, catalysts would be selected for a particular alkylation reaction based on their overall suitability for that reaction. An alternative measurement of catalyst activity suitable for use in this invention would be a comparison of conversion between catalysts at a given base set of operating conditions for the reaction to be conducted. Appropriate comparisons can be made based on conversion rates at the least severe operating conditions appropriate for either of the catalysts being compared. The catalyst with higher conversion at the test conditions would be the more active catalyst and would therefore be selected for the initial bed(s) of the reactor.

Preferably the catalyst used in the first bed(s) of the reactor would be at least 10% more active than the catalyst used in a subsequent bed, based on a comparison of conversion rates at the operating conditions of the first bed of the reactor. Even more preferably, the catalyst used in the first bed(s) would be at least 20% more active for the given reaction than the catalyst used in a subsequent bed. Catalyst selections with 25%, 50%, 75%, 100%, and greater than 100% difference in activity would be useful in this invention.

In one embodiment, the same zeolite would be used for the catalyst in each of the beds, but that zeolite would be treated so as to alter its activity. For example, different binders could be used for formulating the catalyst used in the different beds. Silica used as a binder has been found to result in a higher activity catalyst for aromatics alkylation than alumina. Another example would be steaming or otherwise reducing the activity from the "as-synthesized" level to two different levels, and using the higher activity catalyst for the initial bed(s) in the reactor followed by one or more beds containing the lower activity catalyst. For example, an as-synthesized ZSM-5 may have a very high alpha value, but two batches of the same zeolite could be treated to reduce the respective alpha values such that the alpha value of the first is approximately double the alpha value of the second.

Alternatively, two different zeolites could be used so long as they were selected to place the higher activity formulated catalyst in the initial bed(s)-of the reactor.

It will be recognized that the surprising results herein originate from the concept of staging the catalysts by relative activity levels and that this effect will be obtained with one or more beds of higher activity catalyst followed by one or more beds of lower activity catalyst regardless of the actual number of beds of each catalyst or in the reactor as a whole. Although the examples contained herein refer to a first and second alkylation catalyst for ease of description, it will be recognized by those skilled in the art that this invention applies equally to the use of more than two levels of catalyst activity.

A catalyst suitable for use as the first alkylation catalyst of the invention would be a molecular sieve suitable for use in aromatics alkylation processes, preferably a molecular sieve bound with silica. The first alkylation catalyst would preferably be treated to reduce the alpha number from an as-synthesized alpha value but would generally still have a relatively high alpha number.

An example of one catalyst suitable for use as the first catalyst would be a silica bound ZSM-5 zeolite with relatively high alpha activity compared to that generally preferred for the specific operating conditions.

A preferred first catalyst would be approximately 80% ZSM-5 bound with approximately 20% $SiO_2$. Preferably the ZSM-5 is in the form of small crystals, preferably less than about 0.08 micron in diameter. The $SiO_2/Al_2O_3$ ratio of the ZSM-5 would be less than about 200:1, preferably from about 5:1 to about 200:1, more preferably from about 20:1 to about 100:1, and most preferably from about 50:1 to about 75:1. The $SiO_2$ binder is preferably comprised of between 10 and 90% colloidal silica sol such as Ludox HS-40, more preferably about 50% colloidal silica sol, and between 10 and 90% precipitated silica such as Ultrasil, more preferably about 50% precipitated silica. The catalyst would preferably be prepared by extruding the ZSM-5 with the colloidal silica sol and precipitated silica (water and NaOH can be added to facilitate the extrusion) and drying the extrudate. A preferred shape is 0.15875 cm (⅟16-inch) cylindrical extrudates.

In one preferred embodiment, the dried extrudate is then humidified with a steam/air mixture and is exchanged with 1N ammonium nitrate to remove sodium. The exchange is followed by a water wash with deionized water. The exchange/wash procedure is preferably repeated. The catalyst would then be dried, calcined to about 600 to 1200° F. (about 315 to 650° C.), preferably about 1000° F. (about 538° C.), preferably in nitrogen followed by a mixture of air and nitrogen. The first catalyst would then be steamed to reduce the alpha activity to an alpha value from about 60 to about 200, preferably from about 70 to about 100.

A suitable second catalyst could comprise the same ZSM-5 zeolite, preferably prepared by extruding the ZSM-5 with alumina (water can be added to facilitate the extrusion) to 0.15875 cm (⅟16-inch) cylindrical extrudates, drying the extrudate, calcining the dried extrudate to about 600 to 1200° F. (about 315 to 650° C.), preferably about 1000° F. (about 538° C.), in nitrogen followed by a mixture of air and nitrogen. The second catalyst could then be steamed to reduce the alpha activity to a value less than that of the first catalyst, preferably less than about 60, preferably from about 35 to about 55.

While the selection of different binder materials and steaming to different endpoints was described above, it will be recognized by those of ordinary skill in the art that any selection or treatment method suitable for staging the relative activity of aromatics alkylation catalysts will fall within the scope of this invention.

One embodiment of this invention includes reduction and/or elimination of interstage benzene addition. The use of a higher activity catalyst in the first bed(s) allows for conversion using a lower temperature feed. This would then allow reduction of the interstage quench, further reducing the temperature increase in the first bed(s). Both the reduction in temperature and the increased B/E ratio reduce the production of unwanted byproducts. Alternatively, it may be possible to reduce the overall B/E ratio to the reactor as a whole, thus reducing operating costs associated with recycling aromatics such as benzene back to the process.

In another embodiment, this invention can be a process for the vapor-phase reaction of ethylene with benzene, in a molar ratio of benzene to ethylene from about 5 to about 25, preferably 6 to 7, in a multi-stage alkylation reaction zone having a plurality of series-connected catalyst beds, preferably from 4 to 8 beds. The reaction zone would comprise at least one catalyst bed containing a first alkylation catalyst comprising a molecular sieve, preferably bound with silica binder, and having an alpha value from about 60 to about 200, preferably from about 70 to about 100, and at least one subsequent catalyst bed containing a second alkylation catalyst with an alpha value from about 10 to about 60. The reaction zone would be operated at alkylation conditions including temperature and pressure conditions in which the benzene is in a vapor phase to produce an alkylation product comprising a mixture of ethylbenzene and polyalkylated aromatic components. The alkylation product would be withdrawn from the multistage alkylation reaction zone, the polyalkylated aromatic components would be separated from the alkylation product; and at least a portion of the polyalkylated aromatic component would be supplied along with benzene to a transalkylation reaction zone operated in the vapor or liquid phase under temperature and pressure conditions sufficient to cause transalkylation of the polyalkylated aromatic fraction to produce a transalkylation product having an enhanced ethylbenzene content and a reduced polyalkylated aromatic components content.

A further alternative embodiment would involve alkylation of the aromatic component as described above, except that at least a portion of the separated polyalkylated aromatic components would be recycled to the alkylation reaction zone to cause transalkylation of the polyalkylated aromatic fraction to produce a product having an enhanced ethylbenzene content and a reduced polyalkylated aromatic components content.

EXAMPLES

In order to provide a better understanding of the present invention including representative advantages thereof, the following examples are offered. Examples 1 and 2 will describe the use and performance of two individual catalyst compositions in ethylbenzene production. Example 3 will demonstrate the performance of a reactor using the catalysts of Examples 1 and 2 in sequential beds, and Example 4 will describe the impact of using the design of example 3 with increased throughput. Examples 5, 6, and 7 will provide the results of the individual catalysts in a six-bed reactor and a simulation of the results expected from the application of this invention to that reactor.

Example 1 (Comparative)

Single Catalyst

A catalyst was prepared by extruding ZSM-5, having an average crystal size less than 0.08 micron and a $SiO_2/Al_2O_3$ ratio of approximately 60:1, with alumina (water is added to facilitate the extrusion) to 0.15875 cm (1/16-inch) cylindrical extrudates having approximately 35% alumina, drying the extrudate, calcining the dried extrudate to approximately 1000° F. (about 540° C.) in nitrogen followed by a mixture of air and nitrogen. The catalyst was then steamed to reduce the alpha activity to between 35 and 55.

This catalyst was loaded into all four beds of a four-bed reactor as shown in FIG. 1. Ethylene and benzene were introduced into the reactor with an overall weight ratio of benzene to ethylene (B/E) of 21.6 and a WHSV of 70.8 hr$^{-1}$ based on the combined throughput of benzene and ethylene. The details of the percent of total ethylene input at each stage, the percent of total benzene input at each stage, the inlet temperature at each stage, the resulting product impurity levels, and the decline in catalyst activity are shown in Table 1. It is noted that overall ethylene conversion using fresh catalyst is generally in the 99.8 to 99.95 weight % range.

Example 2 (Comparative)

Single Higher Activity Catalyst

A second catalyst was prepared using the same type of ZSM-5 with approximately 20% silica binder (approximately 50% Ludox HS-40, a colloidal silica sol, with approximately 50% Ultrasil, a precipitated silica. The catalyst was prepared by extruding the ZSM-5 with the Ultrasil and Ludox (water and NaOH were added to facilitate the extrusion) to 0.15875 cm (1/16-inch) cylindrical extrudates, drying the extrudate. The dried extrudate was then humidified with a steam/air mixture and exchanged with 1N ammonium nitrate to remove sodium. The exchange was followed by a water wash with deionized water. The exchange/wash procedure was repeated. The catalyst was then dried, calcined to approximately 1000° F. (about 540° C.) in nitrogen followed by a mixture of air and nitrogen. The catalyst was then steamed to reduce the alpha activity to between 70 and 100.

This catalyst was loaded into all four beds of a four-bed reactor as shown in FIG. 1. Ethylene and benzene were introduced into the reactor with an overall weight ratio of benzene to ethylene (B/E) of 22.0 and a WHSV of 71.9 hr$^{-1}$ based on the combined throughput of benzene and ethylene. For Example 2, the ethylene and benzene feed rate are shown as a percentage of the feed rates in Example 1. Details of the percent of total ethylene input at each stage, the percent of total benzene input at each stage, the inlet temperature at each stage, the resulting product impurity levels, and the decline in catalyst activity are shown in Table 1.

It is noted that Example 2, using the higher activity catalyst, reflects lower concentrations of xylenes, DEB, and heavies in the ethylbenzene product.

Example 3

Staged Catalyst Beds with Constant Throughput

For the purpose of Example 3, the catalyst of Example 2 was loaded into the first 2 beds of the reactor, and the catalyst of Example 1 was loaded into the subsequent 2 beds of the reactor. Again, throughput was held roughly constant with the feed rates again shown as percentages of the feed rates represented by Example 1. The results of this configuration are shown in Table 1. It is noted that, surprisingly, the resulting impurities are significantly lower than those of either catalyst alone.

Example 4

Staged Catalyst Beds with Increased Throughout

In Example 4, the reactor was loaded with catalyst as in Example 3, but throughput of both ethylene and benzene were increased by 17.2% and 3.9% respectively as compared to Example 1. Surprisingly, this increase in throughput did not result in significantly higher impurities or a higher decline in catalyst activity than those shown in Example 1.

The surprising benefits of this invention can either be utilized to improve product purity or to increase reactor capacity. A 10 to 15% increase in reactor capacity has significant economic benefits. Another surprising result is that the catalyst aging rate, expressed in terms of decline in % conversion per month is lower for the combination of catalysts shown in Example 3. In Example 4, the aging rate was higher, but even with significantly higher throughput, the aging rate was not as high as the weighted average of the rates experienced by either catalyst alone.

TABLE 1

Alkylation of Benzene in a 4-Bed Reactor

| | Example | | | |
|---|---|---|---|---|
| | 1 | 2 | 3 | 4 |
| Ethylene Feed Rate | 100.0 | 99.8 | 100.6 | 117.2 |
| Benzene Feed Rate | 100.0 | 101.6 | 100.6 | 103.9 |
| WHSV (hr-1) | 70.8 | 71.9 | 71.3 | 74 |
| Overall B/E (wt.) | 21.6 | 22.0 | 21.6 | 19.1 |
| Bed 1 B/E (wt.) | 53.2 | 56.6 | 76.3 | 61.3 |
| Bed 1 Ethylene (%) | 27.6 | 27.8 | 21.8 | 23.2 |
| Bed 2 Ethylene (%) | 27.2 | 28.7 | 27.0 | 26.2 |
| Bed 3 Ethylene (%) | 27.2 | 28.7 | 30.9 | 27.6 |
| Bed 4 Ethylene (%) | 17.9 | 14.9 | 20.3 | 22.9 |
| Bed 1 Benzene (%) | 68.0 | 71.7 | 77.0 | 74.5 |
| Bed 2 Benzene (%) | 10.9 | 9.8 | 9.5 | 12.6 |
| Bed 3 Benzene (%) | 10.9 | 9.8 | 7.0 | 6.8 |
| Bed 4 Benzene (%) | 10.2 | 8.8 | 6.5 | 6.2 |
| Bed 1 Inlet (° C.) | 404 | 388 | 376 | 371 |
| Bed 2 Inlet (° C.) | 390 | 391 | 380 | 376 |
| Bed 3 Inlet (° C.) | 383 | 393 | 390 | 385 |
| Bed 4 Inlet (° C.) | 396 | 396 | 399 | 391 |
| p- & m-Xylene (ppm) | 1660 | 1500 | 1360 | 1700 |

TABLE 1-continued

Alkylation of Benzene in a 4-Bed Reactor

| | Example | | | |
|---|---|---|---|---|
| | 1 | 2 | 3 | 4 |
| o-Xylene (ppm) | 480 | 420 | 380 | 500 |
| DEB/EB (wt. %) | 26.65 | 24.55 | 21.8 | 25.6 |
| Heavies (ppm) | 3100 | 2600 | 2200 | 2900 |
| Ethylene Conversion Decline (wt. %/mo.) | 0.018 | 0.01 | 0.009 | 0.012 |

Examples 5, 6, and 7

Examples 5 and 6 provide actual data for each of the catalysts of Examples 1 and 2 respectively when used in a six-bed reactor. Example 7 provides a hypothetical example of the staged activity combination of catalysts of this invention when applied to a six-bed reactor, with three beds of the more active catalyst followed by three beds of the less active catalyst. The data for these three examples are presented in Table 2 for comparison.

TABLE 2

Alkylation of Benzene in a 6-Bed Reactor

| | Example | | |
|---|---|---|---|
| | 5 | 6 | 7 |
| Ethylene Feed Rate | 100.0 | 100.6 | 101.7 |
| Benzene Feed Rate | 100.0 | 100.2 | 101.1 |
| WHSV (hr$^{-1}$) | 40.0 | 39.9 | 40.3 |
| Overall B/E (wt.) | 17.3 | 17.2 | 17.2 |
| Bed 1 B/E (wt.) | 67.5 | 90.9 | 105.7 |
| Bed 1 Ethylene (%) | 12.6 | 10.7 | 10.4 |
| Bed 2 Ethylene (%) | 13.8 | 13.9 | 13.5 |
| Bed 3 Ethylene (%) | 15.5 | 15.5 | 16.8 |
| Bed 4 Ethylene (%) | 17.3 | 17.3 | 18.0 |
| Bed 5 Ethylene (%) | 19.4 | 21.1 | 20.4 |
| Bed 6 Ethylene (%) | 21.3 | 21.4 | 21.0 |
| Bed 1 Benzene (%) | 49.2 | 56.6 | 63.7 |
| Bed 2 Benzene (%) | 6.7 | 5.0 | 4.7 |
| Bed 3 Benzene (%) | 9.0 | 10.0 | 6.8 |
| Bed 4 Benzene (%) | 10.4 | 8.0 | 7.1 |
| Bed 5 Benzene (%) | 11.6 | 10.8 | 9.1 |
| Bed 6 Benzene (%) | 13.0 | 9.5 | 8.4 |
| Bed 1 Inlet (° C.) | 372 | 365 | 354 |
| Bed 2 Inlet (° C.) | 378 | 366 | 359 |
| Bed 3 Inlet (° C.) | 382 | 371 | 364 |
| Bed 4 Inlet (° C.) | 383 | 377 | 369 |
| Bed 5 Inlet (° C.) | 385 | 380 | 379 |
| Bed 6 Inlet (° C.) | 388 | 381 | 388 |
| p- & m-Xylene (ppm) | 410 | 390 | 320 |
| o-Xylene (ppm) | 110 | 100 | 80 |
| DEB/EB (wt. %) | 10.5 | 9.0 | 8.0 |
| Heavies (ppm) | 2300 | 2000 | 1650 |
| Ethylene Conversion Decline (wt. %/mo.) | 0.015 | 0.008 | 0.007 |

We claim:

1. A process for alkylating an aromatic hydrocarbon reactant with an alkylating agent to produce an alkylated aromatic product, said process comprising:
   (a) introducing said aromatic hydrocarbon reactant and said alkylating agent into a reactor unit containing a plurality of sequentially arranged beds comprised of a first bed containing a first catalyst effective for alkylating said aromatic hydrocarbon reactant and a second bed downstream from said first bed and containing a second catalyst effective for alkylating said aromatic hydrocarbon reactant and having less catalytic activity than said first catalyst;
   (b) alkylating in said first bed under alkylation conditions said aromatic hydrocarbon reactant with said alkylating agent to form a first effluent comprising a mono-alkylaromatic compound, an unreacted portion of the aromatic hydrocarbon reactant, and polyalkylated aromatic compounds:
   (c) alkylating in said second bed under alkylation conditions at least a portion of said unreacted aromatic hydrocarbon reactant present in said effluent with said alkylating agent to form a product effluent: and
   d) removing said product effluent from said reactor unit, said product effluent comprising a mono-alkylaromatic compound, an unreacted portion of the aromatic hydrocarbon reactant, and polyalkylated aromatic compounds, wherein the first catalyst has an alpha value greater than the alpha value of the second catalyst and wherein the first catalyst and the second catalyst comprise ZSM-5.

2. The process of claim 1, wherein said alkylation conditions within the reaction zone comprise temperature and pressure conditions at which the aromatic hydrocarbon reactant is in a vapor phase.

3. The process of claim 1, wherein the molar ratio of the aromatic hydrocarbon reactant to the alkylating agent is from about 5 to about 25.

4. The process of claim 1, wherein the aging rate of the staged combination of the first and second catalysts is less than the aging rate of either catalyst individually.

5. The process of claim 1, wherein the first catalyst has an alpha value from about 60 to about 200 and the second catalyst has an alpha value from about 20 to about 100.

6. The process of claim 1, wherein the reactor unit comprises from 4 to 8 catalyst beds.

7. The process of claim 1, wherein the first and second catalysts each comprise the same molecular sieve.

8. The process of claim 1, wherein the first and second catalysts each has a crystal size of less than one micron.

9. The process of claim 1, wherein the first catalyst comprises a molecular sieve and a silica binder and the second catalyst comprises a molecular sieve and an alumina binder.

10. The process of claim 1, wherein the aromatic hydrocarbon reactant comprises benzene and the alkylating agent comprises ethylene.

11. The process of claim 10, wherein at least 65% of the total benzene introduced to the reactor unit is introduced in the first bed of the reactor.

12. The process of claim 1, wherein the first catalyst is at least 10% more active than the second catalyst for alkylation of the aromatic hydrocarbon reactant at the operating conditions of the first bed.

13. The process of claim 1, wherein the first catalyst is at least 100% more active than the second catalyst for alkylation of the aromatic hydrocarbon reactant at the operating conditions of the first bed.

14. A process for the vapor-phase ethylation of benzene comprising:
   a) providing a multi-stage alkylation reaction zone having a plurality of series-connected catalyst beds, at least one of the series-connected catalyst beds containing a first alkylation catalyst comprising a zeolite and at least one subsequent catalyst bed containing a second alkylation catalyst comprising a zeolite, the first alkylation catalyst being more active for the ethylation of benzene than the second alkylation catalyst, b) introducing benzene and ethylene into the multistage alkylation reaction zone;

c) operating the multistage alkylation reaction zone at temperature and pressure conditions in which the benzene is in a vapor phase to cause vapor-phase ethylation of the benzene in the presence of the first and second alkylation catalysts to produce an alkylation product comprising a mixture of ethylbenzene and polyalkylated aromatic components; and d) withdrawing the alkylation product from the multistage alkylation reaction zone, wherein the first catalyst has an alpha value greater than the alpha value of the second catalyst and wherein the first catalyst and the second catalyst comprise ZSM-5.

15. The process of claim 14, wherein the feedstock has a benzene/ethylene molar ratio from about 5 to about 25.

16. The process of claim 14, wherein the zeolite in the first catalyst has a silica/alumina ratio from about 5 to about 200 and the zeolite int he second catalyst has a silica/alumina ratio from about 5 to about 200.

17. The process of claim 14, wherein the multistage alkylation reaction zone comprises 4 to 8 catalyst beds.

18. The process of claim 14, wherein the zeolite of the first and second alkylation catalysts each has a crystal size of less than one micron.

19. The process of claim 14, wherein the first alkylation catalyst is at least 25% more active than the second alkylation catalyst for the ethylation of benzene at the operating conditions of the first bed of the reaction zone.

20. The process of claim 19, wherein the first alkylation catalyst is at least 50% more active than the second alkylation catalyst for the ethylation of benzene at the operating conditions of the first bed of the reaction zone.

21. A process for the vapor-phase reaction of ethylene with benzene, the process comprising:

a) introducing benzene and ethylene, in a molar ratio of benzene to ethylene from about 5 to about 25 into a multi-stage alkylation reaction zone having a plurality of series-connected catalyst beds, at least one catalyst bed containing a first alkylation catalyst comprising a molecular sieve bound with silica binder and having an alpha value from about 60 to about 200 and at least one subsequent catalyst bed containing a second alkylation catalyst with an alpha value from about 10 to about 60, wherein the first catalyst and the second catalyst comprise ZSM-5;

b) operating each stage of the alkylation multistage reaction zone at temperature and pressure conditions in which the benzene is in a vapor phase to produce an alkylation product comprising a mixture of ethylbenzene and polyalkylated aromatic components;

c) withdrawing the alkylation product from the multistage alkylation reaction zone;

d) separating the polyalkylated aromatic components from the alkylation product; and e) supplying at least a portion of the polyalkylated aromatic component along with benzene to a transalkylation reaction zone operated in the vapor or liquid phase under temperature and pressure conditions sufficient to cause transalkylation of the polyalkylated aromatic fraction to produce a transalkylation product having an enhanced ethylbenzene content and a reduced polyalkylated aromatic components content.

22. The process of claim 21, wherein the reaction zone comprises from 4 to 8 catalyst beds.

23. A process for the vapor-phase reaction of ethylene with benzene, the process comprising:

a) introducing benzene and ethylene, in a molar ratio of benzene to ethylene from about 5 to about 25 into a multi-stage alkylation reaction zone having a plurality of series-connected catalyst beds, at least one catalyst bed containing a first alkylation catalyst comprising a molecular sieve bound with silica binder and having an alpha value from about 60 to about 200 and at least one subsequent catalyst bed containing a second alkylation catalyst with an alpha value from about 10 to about 60, wherein the first catalyst and the second catalyst comprise ZSM-5;

b) operating each stage of the alkylation multistage reaction zone at temperature and pressure conditions at which the benzene is in a vapor phase to produce an alkylation product comprising a mixture of ethylbenzene and polyalkylated aromatic components;

c) withdrawing the alkylation product from the multistage alkylation reaction zone;

d) separating the polyalkylated aromatic components from the alkylation product; and e) supplying at least a portion of the polyalkylated aromatic component to the alkylation reaction zone of step (a) to cause transalkylation of the polyalkylated aromatic fraction to produce a transalkylation product having an enhanced ethylbenzene content and a reduced polyalkylated aromatic components content.

24. The process of claim 23, wherein the reaction zone comprises from 4 to 8 catalyst beds.

* * * * *